United States Patent [19]

Jones et al.

[11] Patent Number: 4,699,718
[45] Date of Patent: Oct. 13, 1987

[54] ION CHROMATOGRAPHY METHOD AND APPARATUS

[75] Inventors: William R. Jones, Westborough; Allan L. Heckenberg, Milford; Petr Jandik, Hopedale, all of Mass.

[73] Assignee: Millipore Corporation, Bedford, Mass.

[21] Appl. No.: 821,154

[22] Filed: Jan. 21, 1986

[51] Int. Cl.$^4$ ............... B01D 15/08; G01N 30/02
[52] U.S. Cl. ................... 210/659; 210/93; 210/198.2; 422/70; 73/61.1 C
[58] Field of Search .......... 210/656, 659, 198.2; 422/70; 73/61.1 C

[56] References Cited

U.S. PATENT DOCUMENTS

| 3,920,397 | 11/1975 | Small et al. | 210/656 |
| 3,926,559 | 12/1975 | Stevens | 210/656 |
| 3,966,596 | 6/1976 | Stevens et al. | 210/656 |
| 4,073,725 | 2/1978 | Takeuchi et al. | 210/659 |
| 4,314,823 | 2/1982 | Rich, Jr. et al. | 210/656 |
| 4,507,390 | 3/1985 | Huriuchi et al. | 422/70 |

OTHER PUBLICATIONS

"Simultane Bestimmung von einigen anorganischen und organischen Anionen durch ein ionenchromatographisches Drei–Saülen–System", Pimminger, et al., Fresenius Z Anal Chem (1985): 445–450, Springer-Verlag, 1985.

"Ion Exclusion Coupled to Ion Chromatography: Instrumentation and Application", Rich, et al., Ion Chromatographic Analysis of Environmental Pollutants, vol. 2, Ann Arbor Science, Ann Arbor, Michigan (1979), pp. 17–29.

"Organic Acids by Ion Chromatography", Rich, et al., Liquid Chromatography in Clinical Analysis, L. J. Marton, P. M. Kabra, Eds., the Humana Press, Inc., 1981, 393–407.

Primary Examiner—Ernest G. Therkorn
Attorney, Agent, or Firm—Hamilton, Brook, Smith & Reynolds

[57] ABSTRACT

A method and apparatus for the simultaneous analysis of borate and chloride ions in a liquid sample, such as a sample of nuclear reactor water, by ion chromatographic techniques are disclosed. The ion chromatographic system employed includes an exclusion column, an anion exchange column, and means for alternately directing effluent from said exclusion column to refractive index detecting means or void volume from the exclusion column and second eluent through the anion exchange column to conductivity detecting means.

18 Claims, 9 Drawing Figures

ION CHROMATOGRAPHY METHOD AND APPARATUS

FIELD OF THE INVENTION

This invention is in the field of ion analysis and more particularly relates to ion chromatography.

BACKGROUND OF THE INVENTION

An advanced ion chromatographic technique was first reported in 1975 by Small, H., Steven, T. S., and Bauman, W. C., Anal. Chem. 47, 1801 (1975). It was performed in a system consisting of two ion exchange columns connected in series followed by an electrical conductivity detector. A sample was delivered by a stream of flowing eluent to the first ion exchange column. In passing through the column, ions were separated into discrete bands based upon their relative affinity for functional groups on the surface of a pellicular ion exchange resin packed into the column. These discrete bands of ions appearing in effluent from the first (separator) column are thus available for detection, identification and quantitation.

Using only the separator columns, such as those available to Small et al., it is difficult, however, to detect the separated ions at low concentrations because of a poor signal to noise ratio obtainable in the electrical conductivity detector. Because of this, the effluent from the separator column was passed through a second (suppressor) ion exchange column which contained a packing having functional groups of opposite charge to those on the resin in the separator column. The suppressor column functioned to enhance the conductivity signal of the separated bands of ions and simultaneously minimize the background conductivity signal from the eluent.

A new and improved method of ion chromatography utilizing only the separating column of optimized ion exchange capacity connected directly to a conductivity detector was reported in 1979 by Fritz and coworkers. See D. T. Gjerde, J. S. Fritz, and G. Schmuckler, J. Chromatogr. 186 (1979) 509; and D. T. Gjerde, G. Schmuckler, and J. S. Fritz, J. Chromatogr. 187 (1980) 35.

Since the advent of modern ion chromatography, additional techniques and apparatus have been developed to expand its utility to a wider range of ions. For example, the need to quantitate low concentrations of weakly ionized organic acids led to the development of an ion chromatographic separation based upon the principle of ion exclusion. Rich, W., Smith, F., Jr., McNeil, L. and Sidebottom, T., "Ion Exclusion Coupled to Ion Chromatography: Instrumentation an Application", Ion Chromatographic Analysis of Environmental Pollutants(Ann Arbor Science, Ann Arbor, Mich. 1979), vol. 2, p. 17. Moreover, high performance columns, detectors and other hardware have been developed. For example, amperometric and optical detectors have been employed in addition to the classical conductivity detectors. Additionally, suppressor columns and chemistries have been improved.

Despite the rapid development of methods and apparatus, there are still some situations in which it is inconvenient and time consuming to employ ion chromatography for the required analyses. One such instance occurs in the nuclear power industry. If, for example, a pressurized water reactor accident occurs, boric acid, a neutron absorber, is released into the reactor water to control the fissioning process. It is imperative in such accidents to closely monitor borate levels to ensure that the reactor shuts down. Typically, calibration curves and sample analysis for borate must be accomplished in about 2.5 hours. After about 96 hours from the start of such an accident, it is also necessary to analyze the reactor water for additional anions, particularly chloride.

The current technique for chloride analysis in the nuclear power industry employs an on-line ion chromatograph containing pellicular anion exchange resin, a chemical suppression system and a conductivity detector. Borate analysis is accomplished manually using a laboratory ion chromatograph with chemical suppression and a conductivity detector. Samples employed for borate analysis must be diluted prior to injection into the column and total analysis time per sample is around 20 minutes.

Since borate analysis is a partially manual operation, technicians risk exposure to highly radioactive samples. In addition, the run time per sample for borate is considerably longer than desired.

Because of these difficulties, borate analysis is still performed in many cases by titrimetric techniques.

SUMMARY OF THE INVENTION

This invention relates to the simultaneous analysis of weakly ionized anions such as borate, and strongly ionized anions, such as chloride, in a liquid sample by ion chromatography.

Simultaneous analysis is achieved by directing the liquid sample and a first eluent through a chromatographic exclusion column packed with a resin capable of resolving weakly ionized anions in effluent from the exclusion column and passing strongly ionized anions in the void volume from the exclusion column. The void volume from the chromatograpic exclusion column and a second eluent are combined and directed to a liquid chromatographic anion column packed with an anion exchange resin capable of resolving strongly ionized anions in effluent from the anion column. The refractive index of effluent from the exclusion column is detected and monitored as an indication of the quantity of weakly ionized anions in the sample. Conductivity of effluent from the anion column is detected and monitored as an indication of the quantity of strongly ionized anions in the sample.

As used herein, the term "weakly ionized anions" means anions from materials having a pKa higher than about two. Examples of weakly ionized anions are borate, carbonate and anions of carborylic acids. The term "strongly ionized anions" means anions from materials having a pKa less than about two. Examples of strongly ionized anions include chloride, nitrate, and sulfate.

The method of this invention is conveniently carried out in an apparatus designed for the simultaneous chromatographic separation and quantitative analysis of strongly ionized anions in the presence of weakly ionized anions in a liquid sample. The apparatus comprises: a chromatographic exclusion column packed with an exclusion resin capable of resolving weakly ionized anions in effluent from the exclusion column and passing strongly ionized anions contained in the void volume from the exclusion column; a reservoir of first eluent; means for pumping first eluent through the chromatographic exclusion column; sample injection means for injecting the liquid sample into first eluent prior to the time the eluent enters the chromatographic exclusion column; refractive index monitoring means for monitoring the refractive index of effluent from the chromatographic exclusion column; a chromatographic anion column packed with an anion exchange resin capable of resolving strongly ionized anions in effluent from the anion column; a reservoir or second eluent; means for pumping second eluent through said chromatographic anion column; conductivity monitoring means for monitoring the electrical conductivity of effluent from said chromatographic anion column; means for alternately (1) combining void volume from the chromatographic exclusion column with second eluent and directing them to the chromatographic anion column or (2) directing effluent from the chromatographic exclusion column to the refractive index detection means; and control means for operating the means for alternately combining void volume from the exclusion column with second eluent and directing them to the chromatographic anion column or directing effluent from the chromatographic exclusion column to the refractive index detection means.

The method and apparatus of this invention offer several advantages over prior methods and apparatus for detecting anions in the presence of boron, particularly for use in the nuclear power industry. Since no dilution of the sample is required, on-line borate analysis is possible instead of the manual operation now currently being performed. Additionally, borate analysis can be run in much shorter periods of time than is customary, and chloride can be simultaneously analyzed from the same sample. The system is simplified because it does not require any post-column suppression device. Since borate analysis is performed independently from the chloride analysis, multiple borate analyses can be performed while the more time consuming analysis of chloride is in progress. Moreover, the refractive index detector employed for boron analysis provides linearity over a much wider range than other commonly employed detector systems.

BEST MODE OR CARRYING OUT THE INVENTION

As stated above, this invention relates to a method and apparatus for the simultaneous analysis of boron and additional anions in a liquid sample by ion chromatography. It is particularly useful in carrying out an on-line analysis for boron and additional anions in the water employed in nuclear reactors. The boron is often present as borate anion since boron is added in the form of boric acid when an accident has occurred. The additional anions are typically inorganic anions and include such anions as chloride, sulfate, iodide, nitrate, bromide, etc. Of these, it is particularly important in the nuclear power industry to detect the levels of chloride in the presence of boron.

Figure 1:
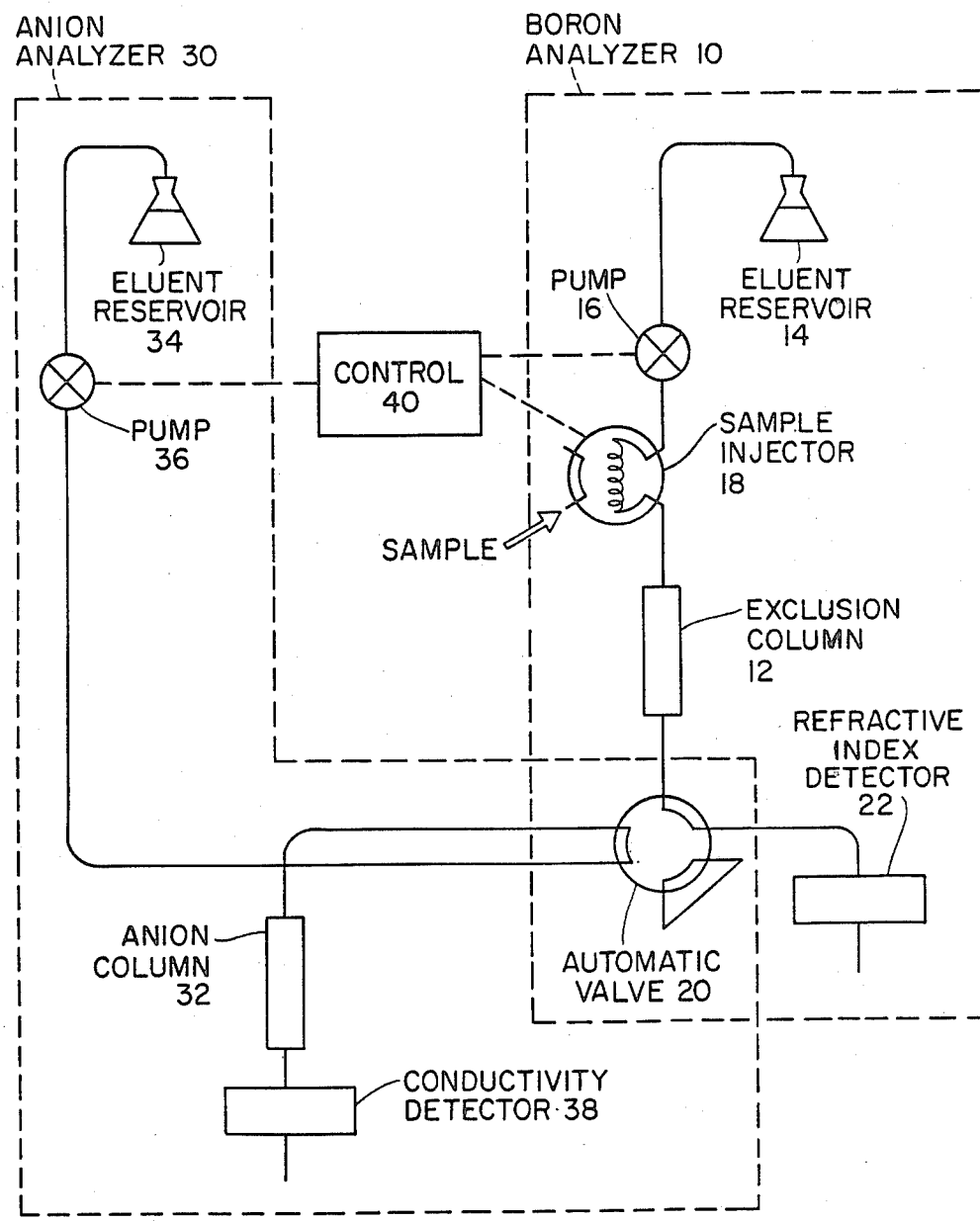
FIG. 1 is a schematic illustration of a simultaneous chloride and boron ion chromatographic system according to this invention.

The method and apparatus are further illustrated by referring to FIG. 1 which illustrates schematically an ion chromatographic separation system according to this invention. Reference numerals therein correspond to elements described below.

Boron analyzer 10 includes a chromatographic exclusion column 12. Column 12 is packed with an exclusion resin on which weakly ionized anions are resolved in the column. Strongly ionized anions pass through the column in void volume. Since boron, present as boric acid, is a weakly dissociated species, boron can be resolved in effluent from column 12. On the other hand, strongly ionized species, such as chloride, will pass through column 12 in void volume. Typical exclusion resins are sulfonated polymers, and a specific suitable material is a sulfonated copolymer of styrene and divinyl benzene.

A first eluent contained in reservoir 14 is employed to elute the sample through column 12. Eluent is delivered from resevoir 14 by pump 16. The first eluent can be a strong acid such as sulfuric, nitric or phosphoric, or a weaker acid such as sulfonic, or salts thereof. Alkyl or aryl sulfonic acids (e.g., octane sulfonic acid) are particularly preferred because they do not contribute any interferring peaks stemming from the exclusion eluent.

A sample is injected into the first eluent stream via automatic sample injector valve 18. Void volume and effluent from exclusion column 12 pass to automatic switching valve 20. Automatic valve 20 is preferably at least a six-port valve, the operation of which will be described further with reference to FIGS. 2-5. Void volume containing unretained anions to be further analyzed is directed into anion analyzer portion 30 of the system. Effluent from exclusion column 12 is directed by automatic valve 20 to refractive index detector 22. The presence and quantity of boron, resolved in exclusion column 12, are determined by detecting and monitoring the refractive index of effluent from column 12 by detector 22.

As previously mentioned, void volume from exclusion column 12, containing the strongly ionized anions to be detected, is directed by automatic valve 20 into the anion analyzer portion 30 of the system. Portion 30 includes a chromatographic anion column 32 packed with an anion exchange resin capable of resolving the strongly ionized anions. Such anion resins are typically polymeric resins having positively charged functional groups thereon. A specific example is a 10 um fully porous polymethyl methacrylate (PMMA) resin functionalized with alkyl substituted guaternary ammonium groups.

Second eluent contained in reservoir 34 is delivered by pump 36 to automatic valve 20. Carboxylic acids or alkyl or aryl sulfonic acids, or salts of these, are examples of eluents suitable for use as a second eluent. In one position, automatic valve 20 directs second eluent from reservoir 34 to anion column 32. In another position, valve 20 directs second eluent to refractive index detector 22 while simultaneously directing void volume from exclusion column 12 to anion column 32 for anion analysis. The excluded anions in the original sample are resolved by the anion exchange resin in column 32 and the presence and quantity of these anions is determined by detecting and monitoring the conductivity of the solution by detector 38.

The system is operated by microprocessor based controller 40, which may be included in one of the pumps.

The flow of eluents and sample through the apparatus of FIG. 1 is further illustrated by FIGS. 2-5.

Figure 2:
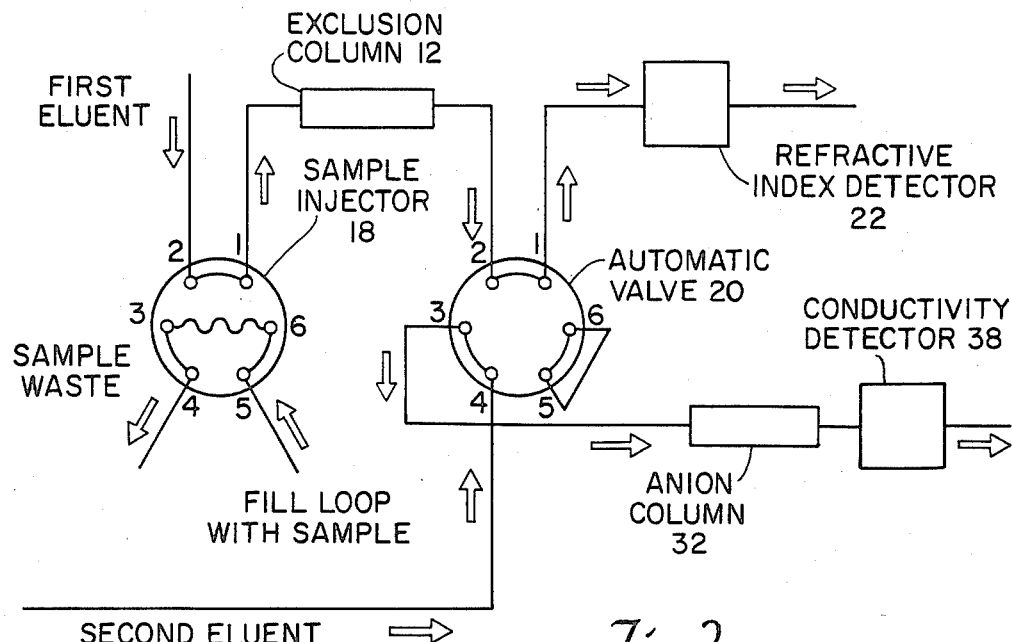
FIGS. 2-5 are schematic diagrams illustrating the flow of sample and eluents through the system of FIG. 1 during a simultaneous analysis for chloride and boron.

FIG. 2 illustrates the initial positions of automatic sample injector valve 18 and automatic switching valve 20, and the flow of first and second eluents, during the sample loading portion of the analysis. As indicated, first eluent is directed through automatic sample injector valve 18 in a manner to bypass the sample loop and is passed directly to ion exclusion column 18 by automatic valve 20. Sample is directed into a suitable sample loop (e.g., 20 or 100 ul) within injector 18. Second eluent is directed by automatic valve 20 directly to anion column 32.

Figure 3:
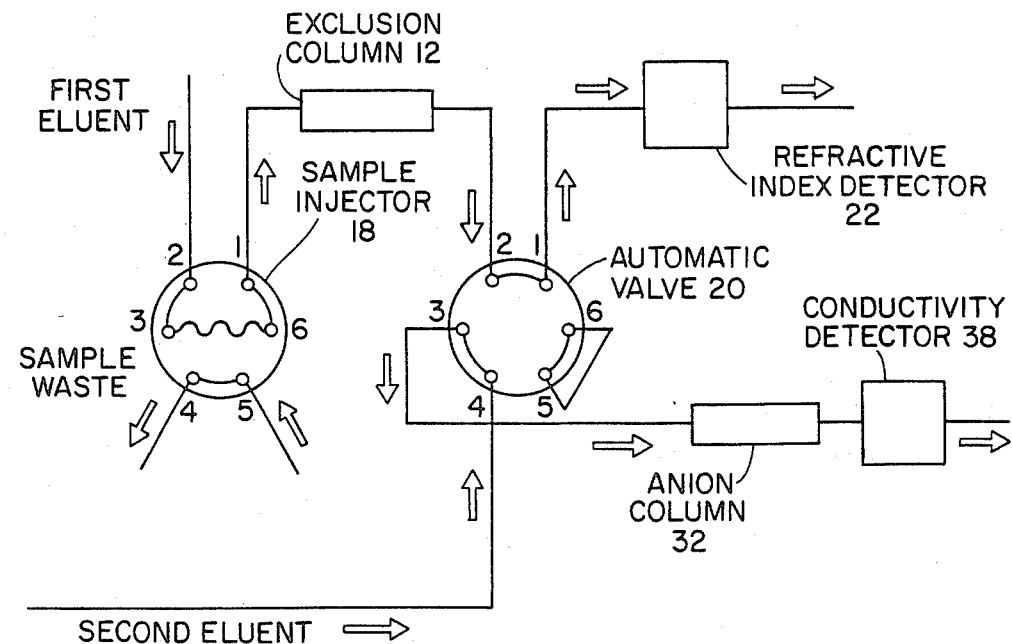

FIG. 3 illustrates the positioning of sample injector 18 and automatic valve 20, and the flow of first and second eluents, during sample injection. As can be seen, the position of sample injector valve 18 has been switched so that first eluent is directed through the sample loop. Thus, the sample originally contained in the sample loop is injected into the eluent carrying it to ion exclusion column 12. The position of valve 20 remains the same as during sample loading. Thus, the sample is eluted with first eluent through ion exclusion column 12 and effluent from column 12 passes through automatic valve 20 to refractive index detector 22.

Figure 4:
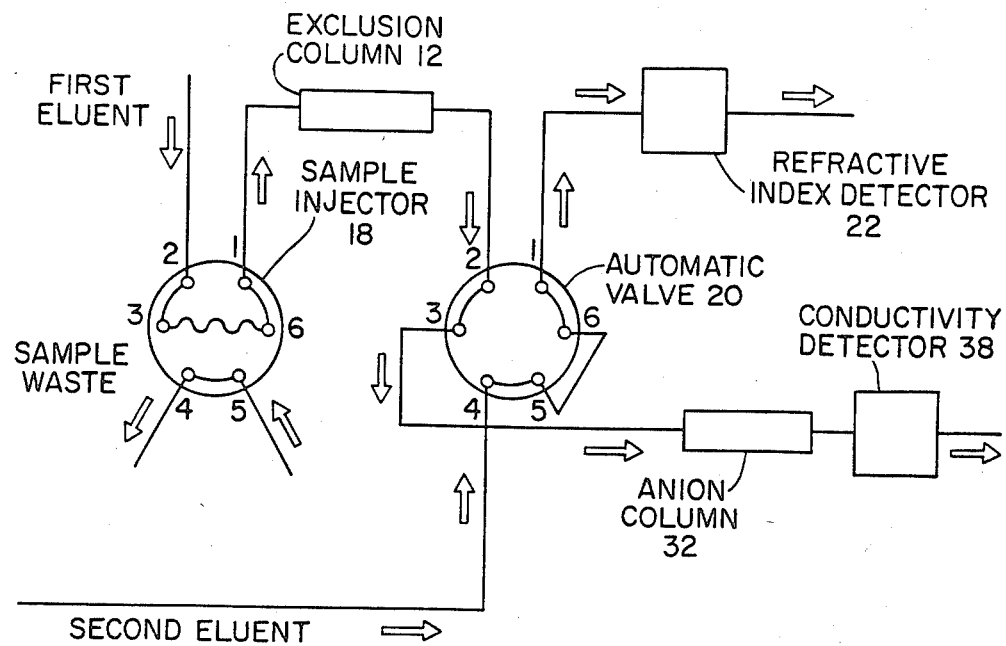

FIG. 4 illustrates the positioning of sample injector 18 and automatic valve 20, and the flow of first and second effluents, during the transfer of strongly ionized anions from the boron analyzer to the anion analyzer. As described above, the strongly ionized anions elute from the anion exclusion column in its void volume. When the void volume reaches automatic valve 20, valve 20 is switched to direct the void volume into anion analyzer 30. Valve 20 thus directs void volume from exclusion column 12 to anion column 32 for resolution of the additional anions. Valve 20 directs second eluent directly to the refractive index detector 22. A loop between ports 5 and 6 is used to allow the second eluent to flow directly to the refractive index detector preventing disturbances of the baseline.

Figure 5:
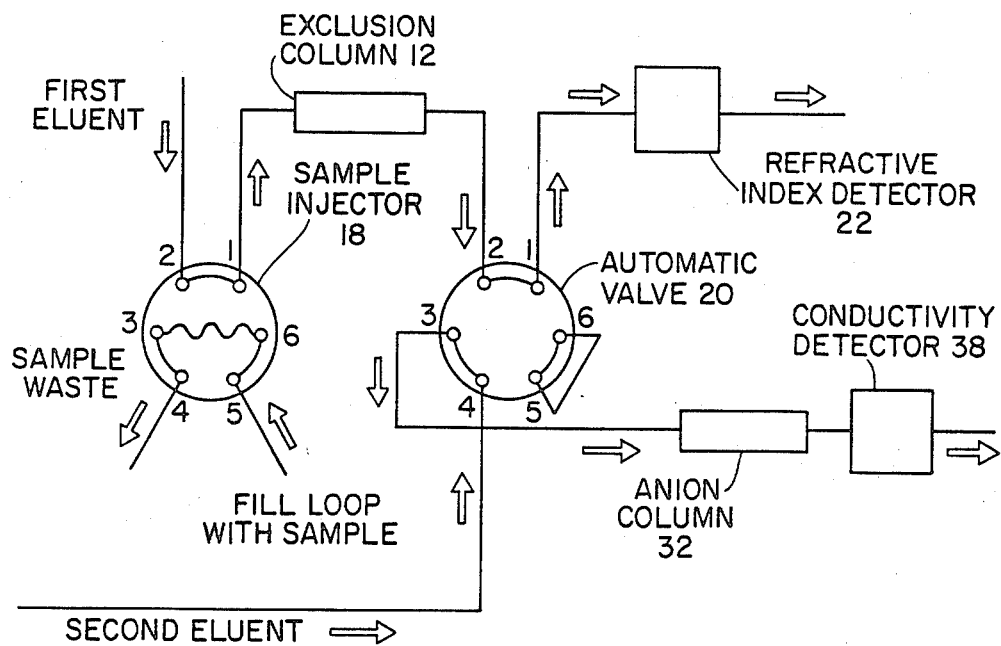

FIG. 5 illustrates the positioning of valves 18 and 20, and the flow of first and second eluents, during analysis of strongly ionized anions. Automatic valve 20 is switched to its initial position reconnecting second eluent with anion column 32 and conductivity detector 38. Effluent from exclusion column 12 is allowed to pass again to refractive index detector 22. Sample injection valve 18 is also returned to its original position to load another sample for subsequent analysis.

The invention is further specifically illustrated by following exemplification.

EXEMPLIFICATION

The apparatus employed to analyze the sample is that illustrated in FIG. 1 employing the following components. The ion exclusion column was a Fast Fruit Juice column marketed by Waters Chromatography Division, Millipore Corporation, Milford, MA. This column was a 7.8 mm×15 cm steel chromatography column packed with a 50 Å, 10micron fully sulfonated resin. The anion exchange column was a Waters I.C. PAK anion column packed with a 10 micron PMMA resin (quaternary ammonium functional groups). The ion exchange capacity of the resin was 30± 3 ueq/ml. The refractive index detector was a Waters 410 Differential Refractometer and the conductivity detector was a Waters 430 conductivity detector. Waters Models 510 and 590 solvent delivery systems were employed. The automatic sample injector valve and automatic switching valve were parts of the Waters Automated Valve Station (WAVS). The control system was a Waters 590 Programmable Module provided with the Model 590 pump.

The reproducibility of boron analyses was tested by making 10 serial injections of three different solutions. The first was a solution of boric acid in water having 2,000 ppm boron.

The second solution (natural pH) was a matrix made up simulating nuclear reactor water after a nuclear accident and formulated according to Nuclear Regulatory Commission regulations. This sample was prepared by dissolving potassium iodide, cesium nitrate, barium nitrate, lanthanum chloride, ammonium cerium nitrate, boric acid and lithium hydroxide in water to provide a sample containing the following anions:

| Constituent | Concentration (ppm) |
| --- | --- |
| Iodide | 40 |
| Cesium | 250 |
| Barium | 10 |
| Lanthanum | 5 |
| Cerium | 5 |
| Chloride | 10 |
| Boron | 2000 |
| Lithium | 2 |
| Nitrate | 150 |
| Ammonium | 5 |
| Potassium | 20. |

The third solution (high pH) was a matrix made up as the natural pH matrix but having its pH raised to 13 by the addition of sodium hydroxide. The latter solution is considered the worst case scenario according to the NRC regulations.

10 mN sulfuric acid was employed as first eluent at a flow rate of 1.0 ml/min. a sample of 100 microliters (1:100 dilution) was injected. The second eluent was 3 mM sodium octane sulfonate at a flow rate of 1 ml/min. The analysis time per sample was 5 minutes.

| 2000 PPM Boron as Boric Acid peak height in cm | natural pH 2000 PPM Boron POST ACC MONITOR peak height in cm | high pH of 13 2000 PPM Boron POST ACC MONITOR peak height in cm |
| --- | --- | --- |
| 1. 20.60 | 1. 20.60 | 1. 20.45 |
| 2. 20.55 | 2. 20.55 | 2. 20.50 |
| 3. 20.55 | 3. 20.60 | 3. 20.60 |
| 4. 20.58 | 4. 20.60 | 4. 20.55 |
| 5. 20.55 | 5. 20.65 | 5. 20.60 |
| 6. 20.60 | 6. 20.60 | 6. 20.60 |
| 7. 20.58 | 7. 20.55 | 7. 20.55 |
| 8. 20.60 | 8. 20.60 | 8. 20.60 |
| 9. 20.55 | 9. 20.60 | 9. 20.50 |
| 10. 20.60 | 10. 20.60 | 10. 20.55 |
| Avg.: 20.58 | Avg.: 20.60 | Avg.: 20.55 |
| Std Dev: 0.024 | Std Dev: 0.028 | Std Dev: 0.053 |

Figure 6:
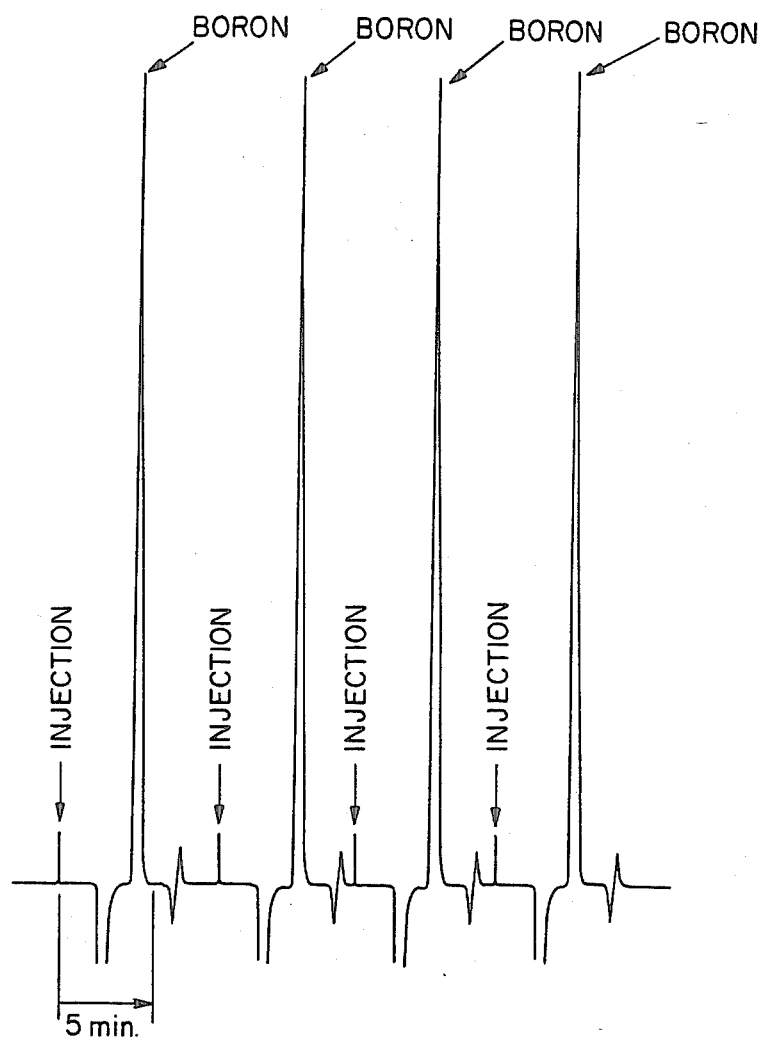
FIG. 6 presents four chromatograms produced by analysis of four serial samples of the same solution containing 2000 ppm boron.

Four out of the ten repeat injections of the boric acid solution produced the chromatograms illustrated at 64% full scale in FIG. 6.

Figure 7:
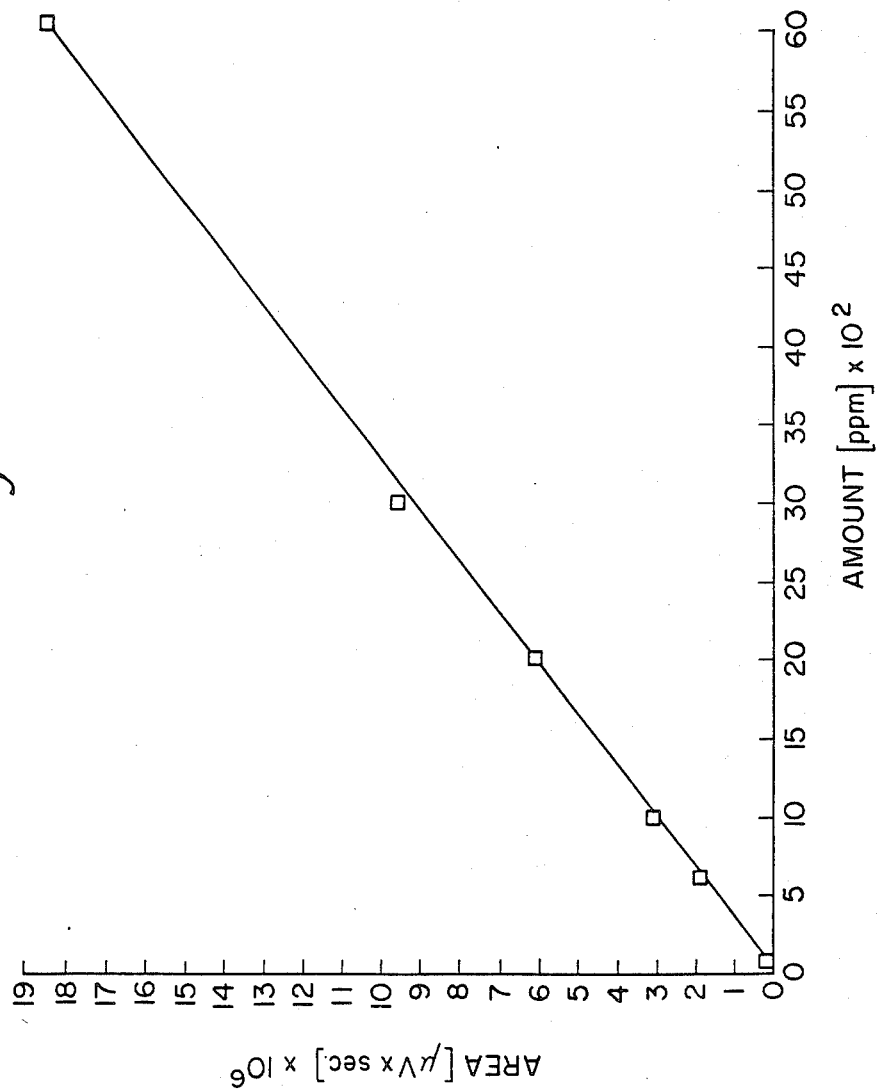
FIG. 7 is a plot illustrating the linearity of boron analysis over widely varying boron concentrations.

The linearity of response in the boron analysis was studied by forming solutions containing 6, 60, 600, 1000, 2000, 3000, and 6000 ppm boron as boric acid in water. 1.25 mN sulfuric acid at a flow rate of 1.0 ml/min. was employed to elute 20 microliter samples. Data handling and processing were done on a Waters 840 system (integration method by areas). The results are shown plotted in FIG. 7 indicating the outstanding linearity over a wide range of boron concentrations.

Figure 8:
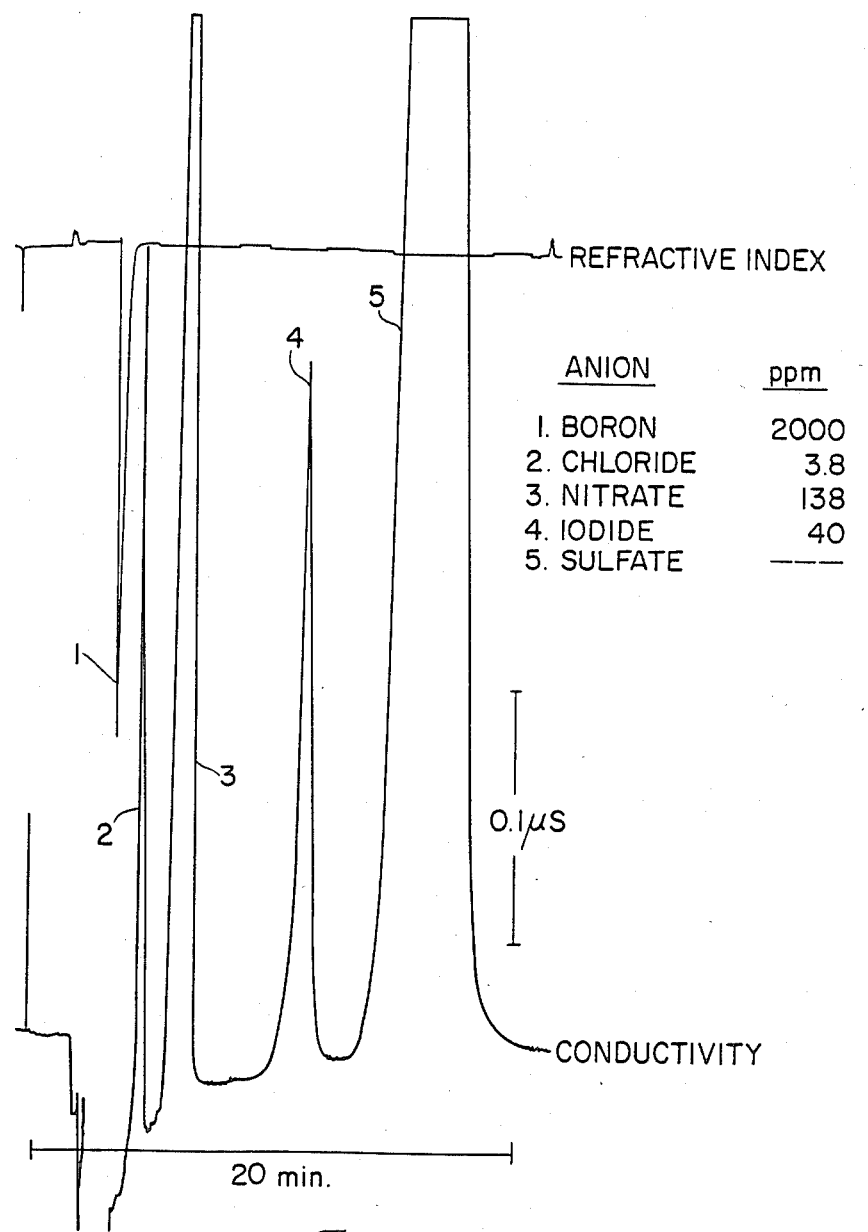
FIG. 8 is a dual chromatogram showing simultaneous analysis for boron and additional inorganic anions.

The system was then employed to detect boron and additional anions simultaneously in the natural pH solution mentioned above. 1.25 mN sulfuric acid at 1.0 ml/min. was used to elute 20 microliter samples 3 mM sodium octane sulfonate was used as a second eluent and 200 microliter void volume cut from the exclusion column was injected to the anion exchange column. Anion analysis required approximately 20 minutes whereas boron analysis required only about 5 minutes. The results are presented in the dual chromatogram shown in FIG. 8.

Figure 9:
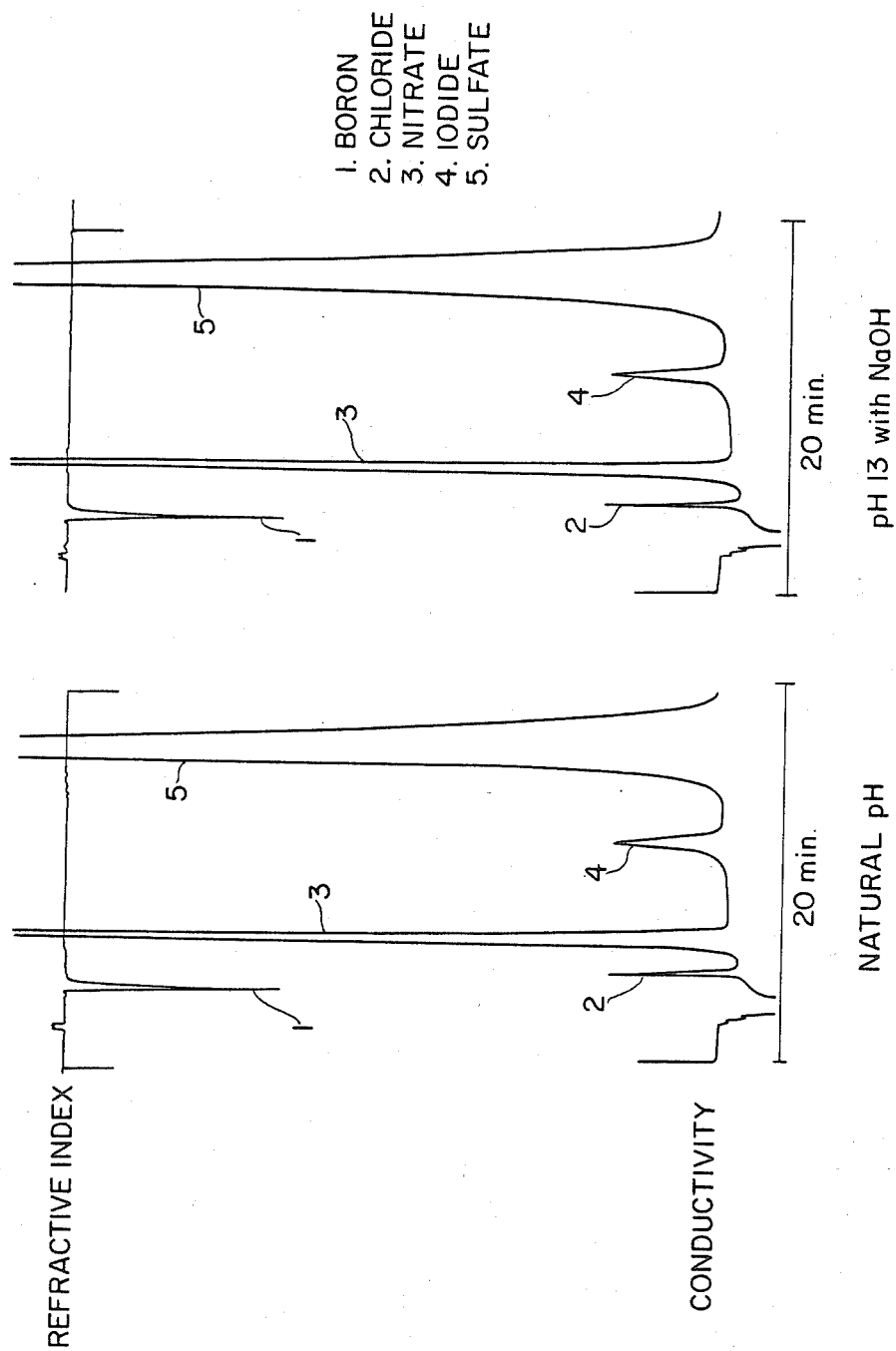
FIG. 9 presents two simultaneous chromatograms produced with boron containing solutions at different pH's to illustrate the pH independence of these analyses.

The effect of pH on sample analysis was then determined. Both the natural pH solution and the high pH solution were employed. The pH independence of sample analysis is illustrated by the two chromatograms which resulted and which are shown in FIG. 9.

A comparison of separations with 3 mM sodium octane sulfonate and borate/gluconate as the anion eluent was then made. The borate/gluconate eluent was prepared by initially formulating a concentrate containing 16 g sodium gluconate, 18 g boric acid, 25 g sodium tetraborate·10H$_2$O, 125 ml glycerine and reagent grade water to make one liter volume. The final eluent was prepared from 15 ml borate/gluconate concentrate, 120 ml acetonitrile, 865 ml water (reagent grade) to form 1,000 ml borate/gluconate eluent.

The use of sodium octane sulfonate resulted in good resolution of chloride, nitrate, iodide and sulfate ions. The borate/gluconate eluent resolved chloride, but nitrate came out of an "acid dip" and sulfate fused with iodide.

Although the method and apparatus of this invention have been described in terms of the separation and quantitation of weakly ionized and strongly ionized anions present in the same liquid sample, other applications are possible with or without modifications to the apparatus or method. For example, the system illustrated herein could also be used for on-line sample preparation. This would be useful, for example, in analyzing for inorganic anions in the presence of concentrated bases, such as sodium hydroxide, or in the presence of concentrated solutions of organic acids.

Further, the system with some modifications, could be employed for the simultaneous analysis of alkali or alkaline earth cations in the presence of strongly ionized anions. Such modifications include the replacement of the exclusion column with a cation exchange column and the replacement of the refractive index detector with a conductivity detector to provide increased sensitivity. In this system, an example of a suitable first eluent for use in the cation exchange column is octane sulfonic acid, whereas an example of a specific eluent for use in the anion column is sodium octane sulfonate.

INDUSTRIAL UTILITY

This invention is useful in analyzing liquid samples containing both strongly ionized and weakly ionized anions by ion chromatographic techniques. It is particularly useful in simultaneously analyzing water employed in a nuclear reactor after a nuclear accident has occurred for the presence of borate and chloride.

EQUIVALENTS

Those skilled in the art will recognize, or be able to ascertain using no more than routine experimentation, many equivalents to the specific embodiment presented herein. Such equivalents are intended to be covered by the following claims.

We claim:
1. A method for the simultaneous chromatographic separation and quantitative analysis of weakly ionized anions and strongly ionized anions in a liquid sample, comprising:
   (a) eluting the liquid sample and a first eluent through a liquid chromatographic exclusion column packed with exclusion resin capable of resolving weakly ionized anions in effluent from the exclusion column and passing strongly ionized anions in void volume from the exclusion column;
   (b) simultaneously eluting void volume containing the strongly ionized anions from said chromatographic exclusion column and a second eluent through a liquid chromatographic anion column packed with an anion resin capable of resolving said strongly ionized anions in effluent from said anion column;
   (c) detecting and monitoring the refractive index of effluent from said exclusion column as an indication of the quantity of weakly ionized anions in the sample; and
   (d) detecting and monitoring the electrical conductivity of effluent from said anion column as an indication of the quantity of strongly ionized anions in the sample.

2. A method of claim 1 wherein said weakly ionized anions include borate.

3. A method of claim 2 wherein said strongly ionized anions include chloride.

4. A method of claim 3 wherein said first eluent comprises an inorganic acid.

5. A method of claim 3 wherein said first eluent comprises an aqueous solution of alkyl or aryl sulfonic acid.

6. A method of claim 5 wherein said second eluent comprises an aqueous solution of a carborylic acid or salt thereof.

7. A method of claim 6 wherein said second eluent comprises an aqueous solution of sodium or potassium alkyl or aryl sulfonate.

8. A method of claim 3 wherein said second eluent comprises an aqueous solution of a carborylic acid or salt thereof.

9. In the quantitative analysis of borate ions and chloride ions in a sample of nuclear reactor water including the steps of resolving the borate ions present in said sample in a first chromatographic separation and resolving chloride ions in a second chromatographic separation:
   the improvement comprising performing both chromatographic separations on-line and simultaneously by:
   (a) eluting a sample of the nuclear reactor water with a first eluent through a chromatgraphic exclusion column under conditions whereby chloride ions in the sample exit the column in its void volume and boric acid present in the sample are resolved in effluent from the exclusion column;
   (b) eluting void volume from said chromatographic exclusion column with a second eluent through a chromatographic anion column under conditions whereby chloride ions in said sample are resolved in effluent from the anion column; and (c) simultaneously monitoring the refractive index of effluent from the exclusion column as an indication of the amount of borate ions in the sample and the electrical conductivity of effluent from the anion column as an indication of the quantity of chloride ions in the sample.

10. The improvement of claim 9 wherein said first eluent comprises an alkyl or aryl sulfonic acid.

11. The improvement of claim 10 wherein said second eluent comprises sodium or potassium alkyl or aryl sulfonate.

12. An apparatus for the chromatographic separation and quantitative analysis of weakly ionized anions and strongly ionized anions in a liquid sample, comprising:

(a) a chromatographic exclusion column packed with an exclusion resing capable of resolving weakly ionized anions in effluent from said exclusion column and passing strongly ionized anions in void volume from said exclusion column;

(b) a reservoir of first eluent;

(c) a means for pumping first eluent through said chromatographic exclusion column;

(d) sample injection means for injection a liquid sample containing weakly ionized anions and strongly ionized anions into first eluent prior to said chromatographic exclusion column;

(e) refractive index monitoring means for monitoring the refractive index of effluent containing weakly ionized anions from said chromatographic exclusion column;

(f) a chromatographic anion column packed with an anion exchange resin capable of resolving strongly ionized anions in effluent from said anion column;

(g) a reservoir of second eluent;

(h) means for pumping second eluent through said chromatographic anion column;

(i) conductivity monitoring means for monitoring the electrical conductivity of effluent containing strongly ionized anions from said chromatographic anion column;

(j) means for alternately directing void volume from the chromatographic exclusion column and second effluent to said chromatographic anion column or directing effluent from said chromatographic exclusion column to said refractive index monitoring means;

(k) control means for operating said valve alternately to direct void volume from said exclusion column and second effluent to said chromatograhic anion column and effluent from said chromatographic exclusion column to said refractive index monitoring means.

13. An apparatus of claim 12 wherein said exclusion resin is capable of resolving boric acid present in said sample.

14. An apparatus of claim 13 wherein said anion exchange resin is capable of resolving chloride ions present in said sample.

15. An apparatus of claim 14 wherein said exclusion resin comprises a sulfonated polymer.

16. An apparatus of claim 15 wherein said sulfonated polymer comprises a sulfonated copolymer of styrene and divinyl benzene.

17. An apparatus of claim 12 wherein said sample injection means comprises means for injecting a sample of predetermined or variable volume.

18. An apparatus of claim 17 wherein said means for alternately directing comprises a valve having at least six ports.

* * * * *